(12) United States Patent
Stanley et al.

(10) Patent No.: US 9,101,350 B2
(45) Date of Patent: Aug. 11, 2015

(54) HALF CANNULA FULL CORE BIOPSY NEEDLE

(71) Applicant: Cook Medical Technologies LLC, Bloomington, IN (US)

(72) Inventors: Cleon Stanley, Bloomington, IN (US); Erik Hughes, Batavia, OH (US); James Taylor, Bloomington, IN (US); Elizabeth A. Theobald, Bloomington, IN (US); Ryan Nowicki, Bloomington, IN (US); Meridith Cavett, Dexter, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/661,361

(22) Filed: Oct. 26, 2012

(65) Prior Publication Data

US 2013/0046201 A1   Feb. 21, 2013

Related U.S. Application Data

(63) Continuation of application No. PCT/US2011/034446, filed on Apr. 29, 2011.

(60) Provisional application No. 61/329,241, filed on Apr. 29, 2010.

(51) Int. Cl.
 *A61B 10/00* (2006.01)
 *A61B 10/02* (2006.01)
 *A61B 17/32* (2006.01)

(52) U.S. Cl.
 CPC . *A61B 10/0266* (2013.01); *A61B 2017/320064* (2013.01)

(58) Field of Classification Search
 USPC ................... 600/564, 567; 604/28
 See application file for complete search history.

(56) References Cited

U.S. PATENT DOCUMENTS

| 4,708,147 | A | 11/1987 | Haaga | |
|---|---|---|---|---|
| 6,033,369 | A * | 3/2000 | Goldenberg | 600/567 |
| 6,080,115 | A * | 6/2000 | Rubinstein | 600/567 |
| 7,914,463 | B2 * | 3/2011 | Tarter et al. | 600/567 |
| 8,012,139 | B2 * | 9/2011 | McKay et al. | 604/506 |
| 2004/0167574 | A1 * | 8/2004 | Kuyava et al. | 606/224 |
| 2007/0142744 | A1 * | 6/2007 | Provencher | 600/562 |

(Continued)

FOREIGN PATENT DOCUMENTS

| WO | WO 03/034915 | 5/2003 |
|---|---|---|
| WO | WO 2007/149302 | 12/2007 |

(Continued)

*Primary Examiner* — Sean Dougherty
*Assistant Examiner* — Daniel Cerioni
(74) *Attorney, Agent, or Firm* — Woodard, Emhardt, Moriarty, McNett & Henry LLP (57) ABSTRACT

There is disclosed, among other things, embodiments of a biopsy needle for taking a full core sample through soft tissue. In the illustrated embodiments, an inner tubular member having a semi-cylindrical distal end is within and slidable with respect to an outer tubular member. A semi-cylindrical channel is in the distal end, as well as a planar end surface. The channel has a set of one or more protrusions or texture, and a complementary set of protrusions or texture are placed on the inside of the outer member so that the sets of protrusions or texture face each other when the distal ends of the members are adjacent each other. Methods for using these embodiments are also described.

14 Claims, 4 Drawing Sheets

(56) References Cited

U.S. PATENT DOCUMENTS

2007/0293788 A1* 12/2007 Entrekin et al. ............ 600/564
2008/0281226 A1* 11/2008 Peters ........................ 600/567
2009/0326412 A1* 12/2009 Pakter ........................ 600/567
2011/0082387 A1*  4/2011 Miller et al. ................ 600/567
2011/0190660 A1*  8/2011 Levy .......................... 600/566

FOREIGN PATENT DOCUMENTS

| WO | WO 2008/115526 | 9/2008 |
| WO | WO 2009/137288 | 11/2009 |

\* cited by examiner

HALF CANNULA FULL CORE BIOPSY NEEDLE

CROSS-REFERENCE TO RELATED APPLICATIONS

The present application is a continuation of International Application No. PCT/US2011/034446, filed Apr. 29, 2011, pending which claims the benefit under 35 USC §119(e) of U.S. Provisional Patent Application Ser. No. 61/329,241, filed Apr. 29, 2010, each of which is hereby incorporated by reference herein.

This disclosure concerns devices for obtaining a tissue sample in biopsy. In particular, it concerns devices able to obtain a full-circular core of tissue with improved results over existing devices.

BACKGROUND

It is often desirable to perform a biopsy to sample selected tissue from a patient for medical evaluation. For example, biopsies can be useful in diagnosing various forms of cancer and other diseases affecting a localized area of tissue. However, many existing biopsy devices use only about half or less of their diameter to obtain tissue. Other devices that obtain a full cylinder or "full core" of tissue have difficulty in withdrawing tissue, and/or in maintaining the physical state of the tissue so as to provide an accurate assessment of tissue condition. With respect to the latter difficulty, one desire in obtaining tissue samples is to obtain the tissue with minimal physical changes, such as from scoring or mashing by the device. Physical characteristics of tissue, such as placement or orientation of cells or tissue, may be as important or more important than the chemical or biological characteristics (e.g. presence of malignant cells or by-products). Existing full-core biopsy needles can physically damage tissue as the sample is being obtained in vivo, and further damage to the sample (e.g. pulling the sample apart) can occur as the sample is pulled or picked out of the needle.

Accordingly, there is a need for a biopsy apparatus and method that are better able to provide samples that are easier to study.

SUMMARY

Among other things, there is shown and described a full-core biopsy needle having an internal cannula or tubular member and an external cannula or tubular member. In particular embodiments, the internal tubular member has a cylindrical proximal portion, a distal portion with a semi-circular cross-section and a lumen along a longitudinal axis through those proximal and distal portions, with the lumen forming a semi-circular channel through the distal portion. The distal portion can include a textured section (e.g. a set of at least one protrusion) in the channel and a U-shaped end surface that is planar and oblique to the axis. The external tubular member is cylindrical throughout and has a lumen extending therethrough and sized to allow the internal tubular member to slide within the external tubular member without substantial play. The external tubular member has a distal portion with a planar end surface that is oblique to the longitudinal axis, and that distal portion may have a textured section (e.g. a set of at least one protrusion) extending into the external tubular member's lumen. When the end surface of the internal tubular member is positioned adjacent the end surface of the external tubular member, the sets of at least one protrusion or other textured sections generally face each other.

In certain embodiments, the internal and external tubular members are non-rotatable with respect to each other around the axis. The semi-circular cross-section in the internal tubular member may subtend an arc of up to about 200 degrees, particularly an arc between about 160 degrees and 200 degrees, and still more particularly an arc of about 180 degrees. A handle can be connected to the internal tubular member and external tubular member so as to move the tubular members with respect to each other to obtain a substantially cylindrical tissue sample. The textured sections or sets of protrusion(s) are each comprised of a substantially helical ridge in some embodiments.

Exemplary biopsy needles for use in sampling soft tissue can include an inner tubular member having a lumen and being within an outer tubular member so that the members are slideable with respect to each other along the longitudinal axis of the inner tubular member. The inner tubular member has an external wall and a semi-cylindrical distal portion that subtends an arc of between about 160 to 200 degrees about the longitudinal axis, so that the lumen is a semi-cylindrical channel in the distal portion. The distal portion has a planar end surface that is U-shaped and a sharpened edge along the intersection of that planar end surface and the external wall. The outer tubular member has a central passage through which the inner tubular member extends, and a distal portion having a planar end surface and a sharpened edge at the intersection of that planar end surface and a wall surrounding the central passage.

Such needles may have a first textured section in the channel of the inner tubular member facing a second textured section in the central passage of the outer tubular member. In particular embodiments, the tubular members have a first relative position in which the inner tubular member's planar end surface is adjacent or coplanar with the planar end surface of the outer tubular member, and in that first relative position, the second textured section faces only the channel of the inner tubular member. The textured sections may each comprise a respective type of projection or texture, such as a plurality of round projections. They may each comprise the same type of texture. A handle can be fixed respectively to the inner tubular member and the outer tubular member to allow them to slide with respect to each other. The inner tubular member is adapted to cut a first part-circular profile and the outer tubular member is adapted to then cut a second complementary part-circular profile to provide a substantially circular profile through tissue.

Methods are also disclosed, including embodiments of methods of taking a percutaneous biopsy that include providing a biopsy needle having an outer tubular member and an inner tubular member having a longitudinal axis, with the inner tubular member being within the outer tubular member and the tubular members being slidable with respect to each other along the axis. The inner tubular member has a lumen along the axis and a distal end portion that is semi-cylindrical, wherein the lumen forms a semi-cylindrical channel within the distal end portion and the distal end portion has a U-shaped end surface through which the channel exits. Methods can further include inserting the needle through the skin to a predetermined location, and cutting a first semi-circular profile into tissue by extending the inner tubular member's distal portion distally from the outer tubular member so that tissue occupies the channel from the end surface along the distal portion of the inner tubular member. A second semi-circular profile is cut into the tissue by moving the outer tubular member forward along the inner tubular member, such second semi-circular profile being substantially complementary to the first semi-circular profile, thereby enclosing a substantially cylindrical tissue portion between the outer tubular member and the distal portion of the inner tubular member in the channel. The needle is withdrawn, and the tissue is removed from the channel, e.g. by extending the distal portion from the outer cannula and inverting the distal portion.

In certain embodiments, the removing includes tapping on the distal portion opposite to the channel to dislodge the tissue in a direction substantially perpendicular to the longitudinal axis. The removing can include maintaining the distal portion in an inverted state for a period sufficient for the tissue to drop out of the channel in a direction substantially perpendicular to said longitudinal axis. All or a portion of such methods can be repeated, for example repeating at least cutting a first semi-circular profile, cutting a second semi-circular profile, withdrawing the needle and removing tissue one or more times so as to take multiple samples.

These and other embodiments present biopsy needles that take a larger, full core of tissue over what some existing devices can obtain, while seeking to maintain not only the biological and chemical nature of the tissue but also the physical integrity. The embodiments provide features for maintaining the tissue in the needle during use, and for easier removal of the tissue from the needle when the biopsy is complete.

DESCRIPTION OF THE ILLUSTRATED EMBODIMENTS

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring generally to the Figures, there is shown an embodiment of a soft-tissue biopsy needle 20. Needle 20 includes an internal member 22, an external member 24, and a handle 26. As will be explained in further detail below, internal member 22 and external member 24 are respectively fixed to parts of handle 26, so that internal member 22 and external member 24 are slidable along each other with a close fit. By having both a "close fit" and slidability, it is meant that there is no substantial separation or gap between members 22 and 24, as by a boss or flange. As seen in the embodiments in the drawings, members 22 and 24 have a close and slidable fit at least along their respective distal ends, and in some embodiments that close and slidable fit extends along all or substantially all of their lengths. Such a configuration maximizes the amount of tissue obtained by a needle of particular outer diameter, by minimizing unused space in the needle, or conversely minimizes the external size of a needle needed to obtain a particular amount of tissue.

Internal member 22 is a straight elongated substantially tubular member or cannula in the illustrated embodiment, having a single lumen 32 throughout the entire length of internal member 22. A proximal portion 34 is a full tube that is at least substantially circular in the illustrated embodiment for ease of use and manufacture, enclosing lumen 32 around its circumference. Proximal portion 34 is fixed to handle 26, as will be further discussed below. A distal portion or tip 36 of internal member 22 is less than a full tube. In the illustrated embodiment, distal portion 36 is a half tube, having a circumference from one side edge 37 to the other side edge 38 that is half of the circumference of proximal portion 34. That is, the outer circumference of distal portion 36 is between about 45 and 55 percent of the outer circumference of proximal portion 34, in particular about 50 percent of circumference B. Put another way, measured in a plane perpendicular to the longitudinal axis of internal member 22, the arc subtended by distal portion 36 is between about 160 and 200 degrees and in particular about 180 degrees, while proximal portion 34 subtends an arc about the longitudinal axis of an entire circle or 360 degrees.

Distal portion 36 of internal member 22 is sharpened at a distal end 39, for example by grinding a surface 40 that is planar and oblique to the longitudinal axis of member 22. In one particular embodiment, the angle of planar surface 40 with respect to the longitudinal axis is 30 to 45 degrees or more. An outer edge 42 is formed at the intersection of surface 40 and the outer circumference of distal portion 36, at least a part of which is sharpened to a degree sufficient to easily penetrate soft tissue, such as skin, subdermal tissue, muscle tissue and/or organ tissue. In the illustrated embodiment, the entire edge 42—that is, the entire intersection of surface 40 and the outer circumference of distal portion 36—is sharpened, and so the entire edge 42 actively separates adjacent tissue portions. Other embodiments may have a smaller portion or discrete portions of edge 42 sharpened, at least at the lowermost or forwardmost part of distal end 36. In particular embodiments, edge 42 comes to or approximately to a sharp or rounded point.

Figure 3:
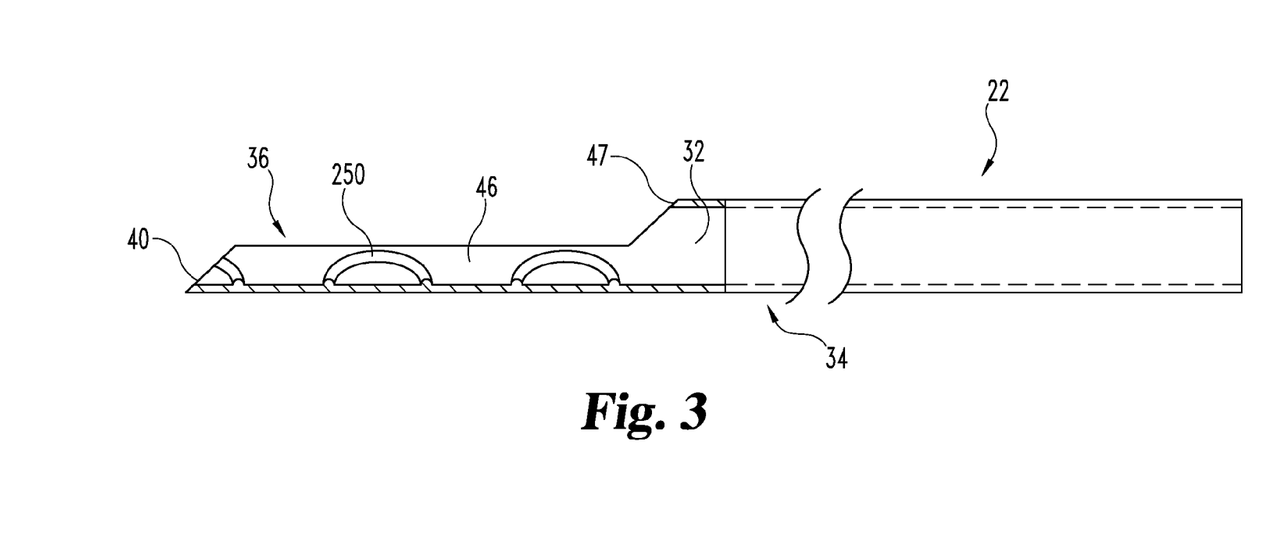
FIG. 3 is a part cross-sectional view of an embodiment of an inner member portion of the embodiment of FIG. 1.

Lumen 32 extends through member 22 continuously with a substantially uniform inner diameter throughout, exiting distal portion 36 of internal member 22 through surface 40. Lumen 32 is sized to be able to accommodate a desired diameter of full-core biopsy material. In particular embodiments, the gage of member 22 is between 10 and 20, such as 16, 18 and 20. The wall thickness of member 22 is preferably thin so as to slice through tissue and present a minimal profile. The minimal profile is found to reduce frictional or blunt-force damage to tissue samples. The portion of lumen 32 in distal portion 36 is a semi-circular channel 46 which biopsy tissue material occupies during use of needle 20. In the illustrated embodiment, the radius of lumen 32 in proximal portion 34 is the same as that of part-circular channel 46 in distal portion 36, with a uniform radius common to both portions. It will be understood that lumen 32 may be of another shape, such as oval or square. Channel 46 evidently has substantially the same circumferential degree measure as distal portion 36 because of the similarly-shaped inner and outer surfaces in the illustrated embodiment. For example, in an embodiment in which the outer surface of distal portion 36 subtends an arc of 180 degrees, the extent of the circumference of channel 46 is also 180 degrees. Inner member 22 also has an edge 47 where surface 40 and inner surface bounding lumen 32 meet. Edge 47 is sharpened in the illustrated embodiment at least along a top portion (above channel 46 as viewed in FIG. 3), and in other embodiments may be sharpened along the entirety of edge 46.

Figure 6A:
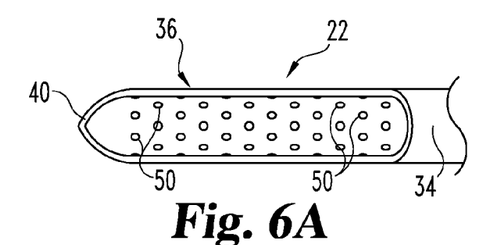
FIG. 6A is a top plan view of a portion of the embodiment of FIG. 1 including an embodiment of holding structure.
Figure 6B:
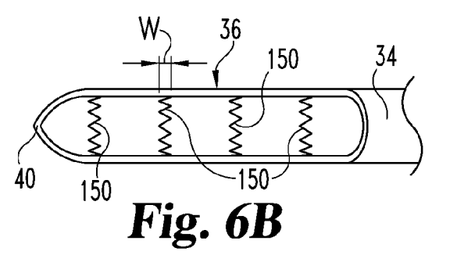
FIG. 6B is a top plan view of a portion of the embodiment of FIG. 1 including another embodiment of holding structure.
Figure 6C:
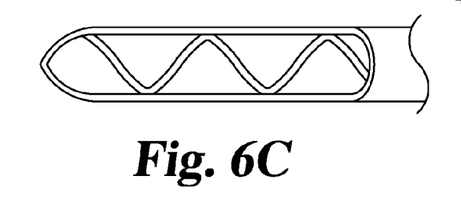
FIG. 6C is a top plan view of a portion of the embodiment of FIG. 1 including another embodiment of holding structure.
Figure 6D:
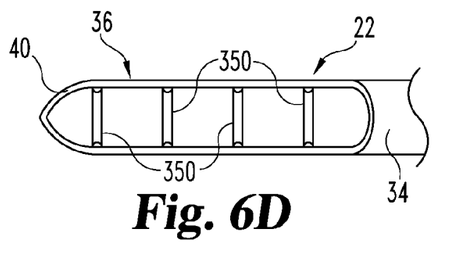
FIG. 6D is a top plan view of a portion of the embodiment of FIG. 1 including another embodiment of holding structure.
Figure 6E:
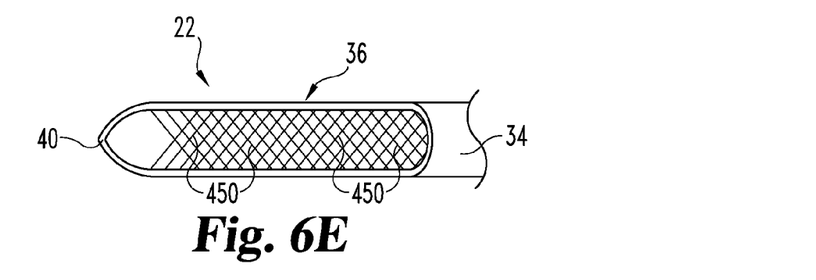
FIG. 6E is a top plan view of a portion of the embodiment of FIG. 1 including another embodiment of holding structure.
Figure 7:
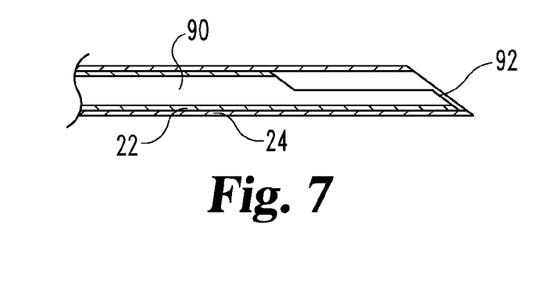
FIG. 7 is a cross-sectional view of a portion of the embodiment of FIG. 1 with additional structure.

Channel 46 and/or a portion of lumen 32 in proximal portion 34 may have projections or texture 50 attached, formed or otherwise provided in a textured section. Texture 50 is intended to supply grip or pull on a tissue sample within channel 46 when needle 20 is withdrawn from the body. In the embodiments of FIGS. 6A-6E, texture or projections 50 are only in channel 46, and may take one or more of a number of forms. In FIG. 6A, projections 50 are a group of substantially round projections or bumps discrete from each other. Projections 50 may be organized in circumferential or helical lines, or may be substantially randomly located on the inside surface of channel 46 of distal portion 36. FIG. 6B shows an embodiment in which projections 150 are a set of zigzagging ridges. In that embodiment, respective ridges move alternately distally and proximally as they move across channel 46, so that there is a width W measured parallel to the longitudinal axis of member 22 between the distal-most and proximal-most parts of the ridge. Respective ridges are evenly spaced from one another in the illustrated embodiment, with a smooth or non-textured portion at least as wide as or wider than the width W of the zigzagging ridges. FIG. 6C shows an embodiment of a projection 250 in the form of a ridge or rib that moves along the surface of channel 46 in a substantially helical path that bends back on itself as it approaches the sides of channel 46. FIG. 6D shows an embodiment in which projections 350 are a set of relatively wide ridges concentric with the longitudinal axis of internal member 22. Respective ridges are evenly spaced from one another in that embodiment, and a non-textured or smooth portion at least as wide as or wider than the width of the respective ridges is found between them. In FIG. 6E, channel 46 is shown as having a number of crisscrossing score lines or thin crisscrossing ridges as texture 450. Such ridges will engage tissue, while score lines will allow fluid or tissue surface to enter the score lines, so that edges of the score lines will help grip or pull the tissue.

Any of the types of projections noted above (or others) may be provided with relatively blunt surfaces or relatively sharp surfaces, or a combination of each. For example, relatively blunt or sloping surfaces may be fashioned on the distal sides or portions of respective projections, and relatively sharp (e.g. perpendicular) surfaces on the proximal sides or portions of respective projections. Insertion of internal member 22 into tissue is not impeded substantially and the tissue sample entering distal portion 36 is not significantly damaged by that insertion, yet the projections dig into or grip the tissue sample if there are forces tending to pull the tissue longitudinally out of distal portion 36. Tissue is thus maintained in channel 46 and sliding of the tissue sample within channel 46 is eliminated or reduced as internal member 22 is withdrawn from the patient.

External member 24 is a complete-tube cannula in the illustrated embodiment, having a proximal portion 60, a distal end 62 and a lumen 64 between those ends. Member 24 is at least substantially circular in the illustrated embodiment, having a cylindrical outer surface 65 and an inner cylindrical surface 66 defining lumen 64, for ease of use and manufacture. Proximal portion 60 is connected to handle 26 so that internal member 22 and external member 24 are movable with respect to each other. Distal end 62 has a planar end surface 68 that is oblique to the longitudinal axis of external member 24. In the illustrated embodiment end surface 68 forms the same angle with the longitudinal axis of external member 24 that surface 40 forms with the longitudinal axis of internal member 22. Thus, when the longitudinal axes of members 22 and 24 coincide, as they do in the illustrated embodiment, surfaces 40 and 68 are parallel or coplanar. Distal end 62 also includes a sharpened edge 70 at the intersection of surface 68 and the exterior circumference of external member 24. The illustrated embodiment of edge 70 is sharpened around its entire length, i.e. around the entirety of external member 24, but in other embodiments only part or parts of edge 70 may be sharpened. The forwardmost or lowermost portion of edge 70 of member 24 may come to a sharp or rounded point.

Lumen 64 of external member 24 is sized and shaped to allow internal member 22 to move within external member 24 along a longitudinal axis shared with or very close to that of external member 24. In the illustrated embodiment, lumen 64 has the same general shape (e.g. circular) in cross-section as the exterior of internal member 22. The internal diameter of lumen 64 is at least slightly larger than the external diameter of internal member 22 so that internal member 22 has a close fit but does not bind with external member 24. The illustrated embodiment shows the internal diameter of lumen 64 to not be substantially greater than the outer diameter of internal member 22 so that there is limited play between members 22 and 24.

Figure 2:
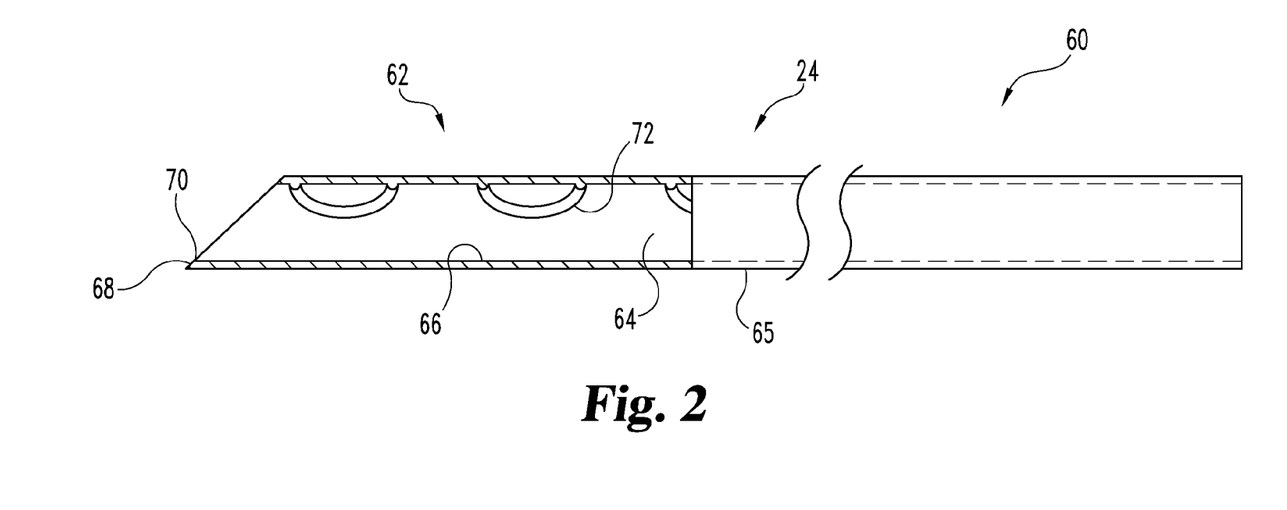
FIG. 2 is a part cross-sectional view of an embodiment of an outer member portion of the embodiment of FIG. 1.

As with channel 46 of internal member 22, the illustrated embodiment of external member 24 includes one or more protrusions or texture 72. As seen in FIG. 2, at least the portion of the inside of external member 24 (in lumen 64) that covers channel 46 when surfaces 40 and 68 are adjacent each other is textured or has protrusions, and the texturing or protrusions is limited to that location within external member 24 in the illustrated embodiment. Protrusions or texture 72 may be any of the types or configurations noted above with respect to protrusions or texture 50, and in the embodiment of FIG. 2 is a rounded ridge 250 that is similar or identical to that shown in FIG. 6C and indicated in FIG. 3 as a part of inner member 22. It will be understood that protrusions or texture 72 (in embodiments that include them) may be the same type as in channel 46 of the corresponding internal member 22, or may be different. That is, if channel 46 includes protrusions 50 as seen in FIG. 6A, protrusions or texture 72 on the wall of lumen 64 may be the same type of texture, or may be a different kind, such as those seen in FIGS. 6B-E.

Figure 4:
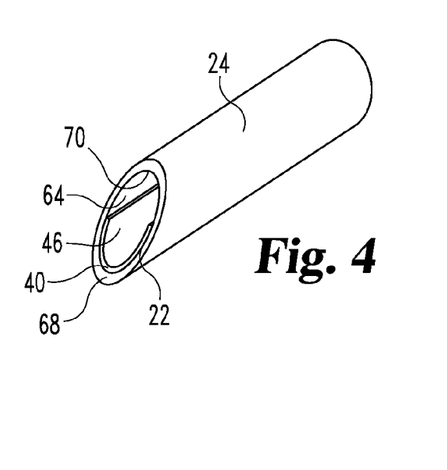
FIG. 4 is a perspective view of a distal end of the embodiment of FIG. 1 in a first insertion state.

Handle 26 in the illustrated embodiment has two rounded finger-holds or grips 82 and a central opening through which members 22 and 24 extend, and in which a spring-loaded firing mechanism (not shown) is placed. An example of handle 26 that may be used in needle 20 is that currently used with QUICK-CORE® products sold by Cook Medical (Bloomington, Ind.). Embodiments of suitable handles are shown in U.S. Provisional Application No. 61/261,857, filed on Nov. 17, 2009, the entirety of which is incorporated herein by reference. Handle 26 is fixed to each of tubular members 22 and 24 at their respective proximal ends, with inner member 22 within outer member 24 and the members being slidable with respect to each other. In this embodiment, plunger 84 is used to move internal member 22 along the longitudinal axis of needle 20 and to fire cocked external member 24 forward, and members 22 and 24 are not rotatable with respect to each other or handle 26 around the longitudinal axis. Such handles 26 permit a cocking step in which the firing of outer member 24 is primed or prepared, an insertion step in which the member 22 is extended from member 24 into the body, and a firing step in which external member 24 is released to move forward rapidly over inner member 22 so that surfaces 40 and 68 are adjacent or aligned (e.g. FIG. 4). The cocking step is performed by holding finger grips 80 and pulling back on plunger 82. Extending member 22 from member 24 is accomplished while holding finger grips 80 by moving plunger 82 forward until plunger 82 is stopped by the cocking mechanism. Firing cannula 24 is accomplished by pushing forward plunger 82 to overcome the resistance of the cocking mechanism, and may be accomplished by the same hand that holds finger grips 80.

Outer member 24 and inner member 22 are slidable with respect to each other, as indicated above. Inner member 22 extends from its connection with handle 26 through the lumen of outer member 24. In a particular embodiment, the outer diameter of inner member 22 is approximately the same as the inner diameter of outer member 24, so that there is little play or space between members 22 and 24, yet they can move smoothly with respect to each other.

A stylet 90 of approximately the diameter of lumen 32 may be inserted through lumen 32 to block lumen 32 from the entrance of substantial tissue prior to needle 20 approaching the tissue to be sampled. Stylet 90 is a rod or wire of an outer diameter substantially the same as the inner diameter of lumen 32 of member 22. A tip end 92 is configured to assist in moving needle 20 through the body, as discussed further below. Accordingly, tip 92 can be sloped like surfaces 40 and/or 68.

Figure 1:
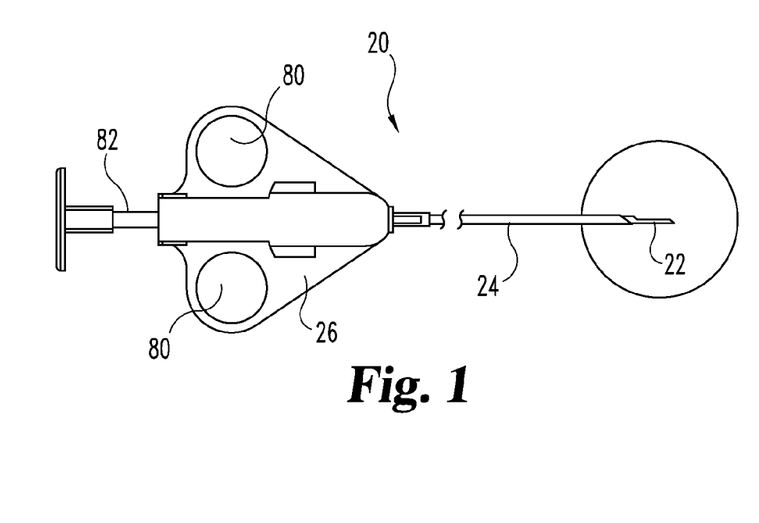
FIG. 1 is a plan view of an embodiment of a biopsy needle.
Figure 1A:
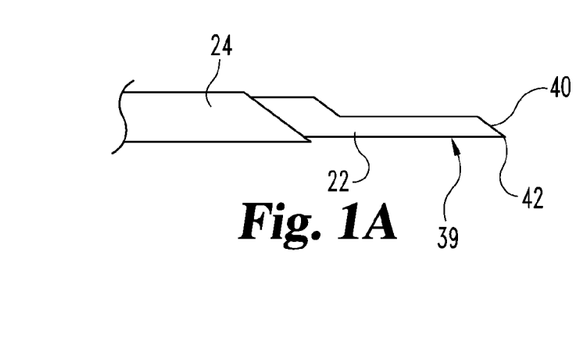
FIG. 1A is a close-up view of a portion of the embodiment of FIG. 1.
Figure 5:
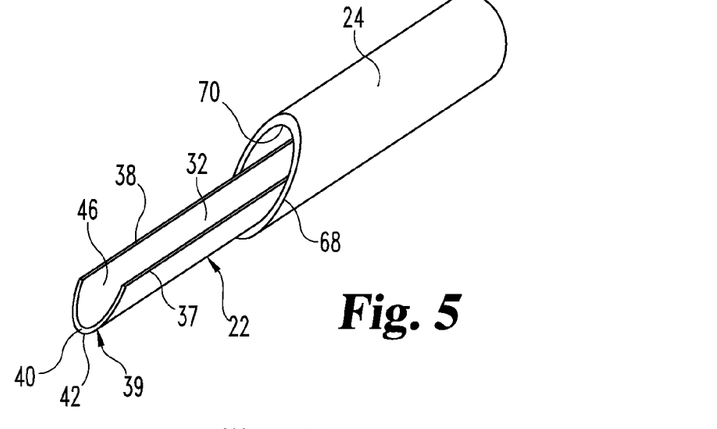
FIG. 5 is a perspective view of a distal end of the embodiment of FIG. 1 in a second extension state.

Members 22 and 24 have a first relative position (e.g. FIG. 4) which is seen before pushing member 22 out of member 24, or after firing needle 20. In that first relative position, oblique surfaces 40 and 68 are adjacent each other, and in the illustrated embodiment are substantially coplanar. In the illustrated embodiment, the opening of lumen 64 of member 24 is elliptical or oblong due to the circularity of lumen 64 and the oblique orientation of surface 68, and surface 68 bounds an elongated U-shaped end of channel 46 of member 22 for the same reason. When member 24 is withdrawn relative to member 22 (or member 22 is moved forward relative to member 24) from that first relative position, members 22 and 24 have a second relative position that corresponds to the pre-fired state of needle 20 (e.g. FIGS. 1, 5). In that second relative position, in the illustrated embodiment, all or substantially all of end portion 36 of member 22 extends out of member 24, and surface 68 of member 24 is at or proximal of edge 47 of member 22.

The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. Handle 26 is cocked so that, in one embodiment, members 22 and 24 are in the relative position of FIG. 4, with end surface 40 flush with or just inside end surface 68 and stylet 90 within lumen 64 and channel 46 and potentially extending slightly from members 22 and 24. In that state, the medical professional places the distal end of needle 20 against the skin at a place proximate to the desired location, and inserts needle 20. Edge 42, in some embodiments assisted by surfaces 40 and 68 and the tip of stylet 90, forces a path through the skin and subcutaneous tissue to a point in or just before the location from which a sample is to be taken. Insertion in this way results in little or no tissue being forced into either lumen 32 of internal member 22 or lumen 64 of external member 24, because of the presence of internal member 22 and stylet 90 in lumen 64. If such a stylet is used, it is withdrawn from at least channel 46 or more of lumen 32 of member 22 prior to obtaining the sample.

When needle 20 is in the correct location, with end surfaces 40 and 68 in or adjacent to the tissue to be sampled, plunger 82 is moved forward to extend internal member 22 from the end of external member 24. If stylet 90 is present, it may be withdrawn (as noted above) or held with respect to inner member 22, so that as internal member moves forward into the tissue to be sampled stylet 90 does not move into the tissue as well. Sharpened edge 42 of inner member 22 cuts a semi-circular profile into the tissue to be sampled as internal member 22 is extended. Distal end 36 is within that semi-circular profile, and tissue fills at least a part of the length of channel 46. In the illustrated embodiment, internal member 22 is not extended from the end of external member 24 beyond the length of distal portion 36, so that only the semi-circular distal portion 36 extends from external member 24, and tissue does not extend substantially into the enclosed portion of lumen 32 of inner member 22. In embodiments in which distal portion 36 is shorter than the extension length of internal member 22 from external member 24, the sampled tissue may extend into lumen 32. Where channel 46 includes protrusions or texture 50, such protrusions or texture 50 engage the tissue sample within channel 46.

When internal member 22 has been extended as desired and the tissue sample rests in channel 46, external member 24 is fired. Pressing plunger 82 forward releases a spring to shoot external member 24 forward so that its end 68 is again adjacent or coplanar with surface 40 of internal member 22. The lower half of external member 24 moves along essentially the same path or profile cut by internal member 22, and its upper sharp edge 72 cuts the tissue in a semicircular profile (in the illustrated embodiment) to complete the circular shape of the profile begun by internal member 22. The upper portion of external member 24, adjacent end surface 68, cuts a complementary half-circle to separate the full-core sample from laterally surrounding tissue. As the illustrated embodiment of needle 20 suggests, such a full-core sample may have a length that is several times its diameter.

The tissue sample is held in channel 46 by distal end 36 of internal member 22 and the overarching wall of external member 24. In embodiments having textures or protrusions 50, 72, 150, 250, 350, 450 in the distal ends of the respective members 24 and 22, such textures present additional friction and/or some pressure on or interference with the tissue in channel 46 to help maintain the tissue in place after the external member 24 is shot forward. Needle 20 is then carefully withdrawn from the patient. Friction between the internal surfaces of members 22 and 24 and the tissue sample pull the sample free of other tissue. Any remaining axial connection of the small diameter of the tissue sample, particularly in comparison to its length, can be overcome by careful withdrawal, and such friction or pulling force is enhanced in embodiments having protrusions or texture to grip the tissue sample between members 22 and 24.

Once needle 20 has been withdrawn from the body, the tissue sample is removed and from needle 20. The configuration of internal and external members 22 and 24 make the removal of a tissue sample much easier than it is in current biopsy needles. The internal member 22 may be again extended from the external member 24 (or the external member 24 may be retracted) to expose distal portion 36 of internal member 22 and the tissue sample within it. With distal portion 36 so exposed, a stylet, probe, forceps or other gripping tool, or similar device can be used to push the tissue sample out of distal portion 36 or to lift it out of channel 46. For example, stylet 90 can be inserted into or behind the tissue sample at about the location where distal portion 36 meets proximal portion 34, and by moving stylet 90 along channel 46, the tissue sample can be pushed along channel 46, past surface 40 and into a sample dish or other receptacle. Because channel 46 is semi-circular or approximately semi-circular, its upper dimension is the same or approximately the same as the diameter of lumen 32, and so stylet 90 having an outer diameter about the same as the inner diameter of lumen 32 will not be too wide to insert into channel 46 from the top and push the tissue sample out of channel 46. Alternatively, the configuration of needle 20 allows the person extracting the tissue sample to simply invert needle 20 over a receptacle. With the tissue sample and channel 46 facing down, the sample falls out of channel 46, or if necessary the user can tap or shake distal portion 36 to cause the tissue sample to drop from channel 46 into the receptacle. Texture or protrusions in any of the embodiments noted above (if present) affect motion of tissue along the longitudinal axis of channel 46, but neither they nor sides 37, 38 of channel 46 impede tissue from falling out of the open top of channel 46. Many partial core biopsy needles, as well as needles that have full- or near-full-circumference tubes, do not permit such ease of removal of the tissue sample.

The ease of removal of tissue samples allows not only uncomplicated use by the physician, analyst or other professional, but also makes the acquisition of multiple samples with the same needle 20 much easier. Once a first sample is taken, needle 20 is easily unloaded and readied to take another sample, from the same location or a different location in the patient. Where some existing devices require involved steps to extract tissue, embodiments of needle 20 can be used once, the sample can be dropped, tapped or pushed out, and needle 20 readied (e.g. recocked) for reuse. The time and effort needed to acquire multiple tissue samples for analysis is reduced.

Internal and external members 24 may be made of any of a variety of rigid biocompatible materials, or others that will not spoil or taint the tissue sample, such as stainless steel. Other embodiments may use appropriately sturdy flexible materials for at least part of one or both of the members, although it will be understood that performance may suffer if such flexible materials do not permit easy advancement of internal member 22 or external member 24. In particular embodiments, distal portion 36 may have a standard length, such as 10 millimeters or 20 millimeters, or may have lengths determined by patient need or usefulness in a particular part of the body.

It will also be understood that needle 20 may be placed through another access device (not shown) that is in, adjacent or on the way to a tissue area to be sampled. For example, an outer needle or sheath (not shown) may be inserted percutaneously through the skin, subdermal tissue, and or other tissues, with needle 20 being inserted through the outer needle or sheath. Operation of needle 20 as indicated above, with needle 20 being advanced through additional tissue if needed, can then take place.

With distal portion 36 being about half of the circumference of proximal portion 34, as in the illustrated embodiment, an optimal sample-cutter is provided which is particularly enhanced when the entire edge 42 is sharpened as in the illustrated embodiment. When a cutting portion of substantially more than half of the circumference is provided, it tends to bind with the tissue being cut and impede the progress of the needle. Even in cases in which the cutting portion is about two-thirds of the circumference the partial encirclation of the tissue creates opposing lateral forces that press tissue together, with resulting reaction of pressure of the tissue on the cutting portion. Further, reducing the length or circumference of the cutting edge 42 allows easier passage of the distal portion 36 as compared to full-circumferential or similar cutting portions, while maintaining a receptacle in distal portion 36 that holds and reduces the chance of accidental spillage or release of tissue within distal portion 36.

As noted above, in some embodiments internal member 22 and external member 24 are non-rotatable with respect to each other. It is also contemplated that members 22 and 24 are connected with handle 26 so that they are rotatable with respect to each other. For example, external member 24 may be rotated around a stationary internal member 22. Of course, it will be seen that both members may be rotatable at least to a degree, or external member 24 may be stationary as internal member 22 turns inside it.

Embodiments in which one or both of members 22, 24 are rotatable with respect to each other and/or to handle 26 may operate identically or substantially as discussed above. For instance, the member(s) 22 and/or 24 can be arranged to rotate or pivot as they move forward. As external member 24 is released to shoot forward, in some embodiments it can rotate around internal member 22. Such motion can assist in the cutting of the complementary profile and in gripping the tissue sample, insofar as the forward edge moves across the face of tissue in addition to driving forward through it, and insofar as the protrusions in external member 24 are wound along and into the surface of the sample.

Figure 8A:
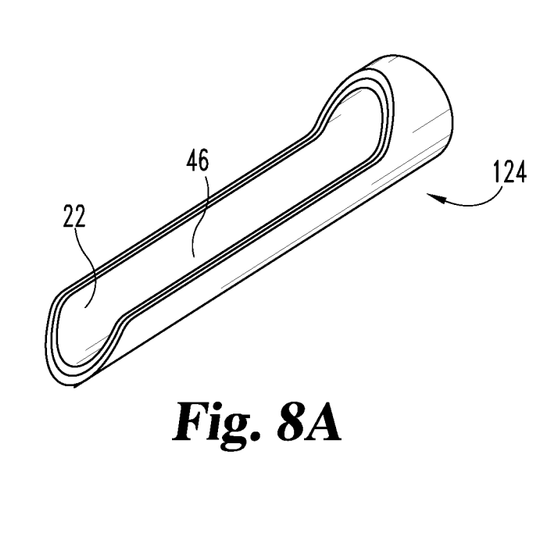
FIG. 8A is a perspective view of a distal end of a similar embodiment of a biopsy needle in a first insertion state.

FIG. 8A shows an embodiment in which an external member 124 is essentially identical with external member 24, except that the distal end 136 of external member 124 is configured similarly or identical to that of internal member 22. Thus, distal end 136 of external member 124 is approximately half-tubular, e.g. having a circumference from one side edge to the other side edge that is half of the circumference of a proximal portion of external member 124. An outer circumference of distal portion 136 can be between about 45 and 55 percent of the outer circumference of such a proximal portion, such as about 50 percent of that circumference. As with external member 24, projections or ridges 50, 150, 250, 350, 450 or in other embodiments may be in the interior of distal end 136 so as to be complementary to such projections or ridges in internal member 22.

A combination of internal member 22 with external member 124 can operate substantially as described above with regard to members 22 and 24, with insertion in a cocked position so that when member 124 is shot forward, a complete or mostly complete profile is cut through tissue. Alternatively, rather than cocking to position members 22 and 124 as shown above, i.e. with the end of member 22 forward of the end of member 124, an embodiment may be inserted with both distal semi-circular (or otherwise similar) ends aligned with each other, i.e. with distal end 36 of member 22 within and/or substantially coinciding with distal end 136 of member 124.

Figure 8B:
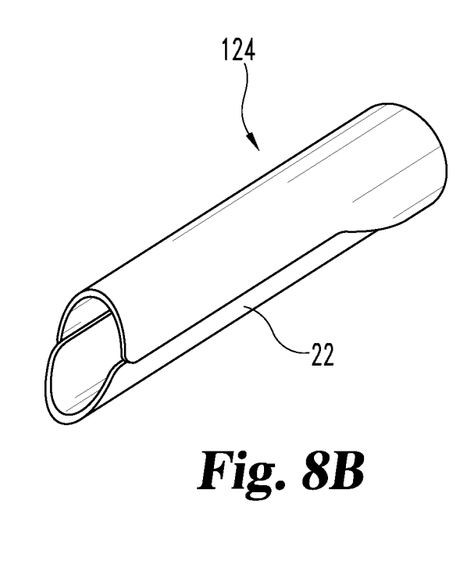
FIG. 8B is a perspective view of a distal end of the embodiment of FIG. 8A in a second state in which one or both members are rotated with respect to each other.

Both members are inserted together into the body, as indicated above, until some or all of channel 46 of member 22 (with end 136 of member 124 beneath it) is within the tissue area desired to be sampled. When so placed, on or both of members 22 and 124 are rotated with respect to each other and/or with respect to handle 26. Side edges of one or both distal ends 36, 136 of members 22, 124 may be sharpened in order to make rotation through the tissue easier and less traumatic to the tissue. Turning one or both members 22, 124 (e.g. to the position indicated in FIG. 8B) cuts the remainder of the profile (circular or otherwise) radially to define a full-core tissue sample. In particular embodiments, once the full profile is cut, members 22, 124 become locked or otherwise inhibited against some or all rotation with respect to each other, so that the risk of losing the tissue sample on withdrawal of members 22, 124 is reduced. Withdrawal from the patient is as discussed above, with the texture or protrusions in each member 22, 124 helping to hold or pull the sample out in embodiments that include them.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected.

What is claimed is:

1. A biopsy needle for use in sampling soft tissue, comprising:
    an inner tubular member having a lumen and being within an outer tubular member so that said members are slideable with respect to each other along the longitudinal axis of the inner tubular member,
    said inner tubular member having an external wall and a semi-cylindrical distal portion that subtends an arc of between about 160 to 200 degrees about the longitudinal axis so that said lumen is a semi-cylindrical channel in said distal portion, said distal portion having a planar end surface that is U-shaped and a sharpened edge along the intersection of said planar end surface and said external wall having a sharpened forwardmost portion adapted to puncture tissue;
    said outer tubular member having a central passage through which said inner tubular member extends, and a distal portion having a planar end surface and a sharpened edge at the intersection of said planar end surface of said outer tubular member and a wall surrounding said central passage, said wall surrounding said central passage that is proximal of the planar end surface of said outer tubular member and opposite said semi-cylindrical distal portion of said inner tubular member having no opening therethrough communicating with said central passage;
    said biopsy needle further comprising a first textured section in said channel of said inner tubular member, said first textured section having an inward facing surface with one or more raised protrusions extending from the inward facing surface toward the lumen, said first textured section facing a second textured section in said central passage of said outer tubular member, said second textured section having a continuous unbroken external surface.

2. The needle of claim 1, wherein said inner tubular member and said outer tubular member have a first relative position in which said planar end surface of said inner tubular member is adjacent or coplanar with said planar end surface of said outer tubular member, and wherein said second textured section is positioned in said outer tubular member so that all of said second textured section faces only said channel when said tubular members are in said first relative position.

3. The needle of claim 2, said second textured section having an inward facing surface opposite the external surface with one or more raised protrusions extending from its inward facing surface toward the lumen, wherein the one or more raised protrusions of said first textured section and the one or more raised protrusions of said second textured section each comprise a respective plurality of round projections, said projections of said first textured section projecting into said channel of said inner tubular member, and said projections of said second textured section projecting into said central passage of said outer tubular member without extending through the external surface of the second textured section.

4. The needle of claim 1, wherein said first textured section and said second textured section each comprise a same type of texture.

5. The needle of claim 1, further comprising a handle fixed respectively to said inner tubular member and said outer tubular member to allow said tubular members to slide with respect to each other, said handle having a pair of finger holds on opposite sides of said tubular members and a plunger operatively connected to the inner tubular member to move the inner tubular member within the outer tubular member.

6. The needle of claim 1, wherein said inner tubular member is adapted to cut a first part-circular profile and said outer tubular member is adapted to then cut a second complementary part-circular profile to provide a substantially circular profile through tissue.

7. The needle of claim 1, wherein the entire edge along the intersection of said planar end surface and said external wall of said inner cannula is sharpened.

8. The needle of claim 3, wherein the one or more raised protrusions of said first textured section and the one or more raised protrusions of said second textured section face each other.

9. The needle of claim 1, wherein the one or more raised protrusions of said first textured section comprise a rounded ridge.

10. The needle of claim 9, wherein the rounded ridge extends along the inward facing surface of the inner tubular member in a helical path.

11. The needle of claim 1, wherein the one or more raised protrusions of said first textured section comprise a set of zig-zagging ridges.

12. The needle of claim 11, wherein adjacent ones of the set of ridges are evenly spaced along a longitudinal distance within the inner tubular member.

13. The needle of claim 1, wherein the one or more raised protrusions of said first textured section comprise criss-crossing ridges.

14. The needle of claim 1, wherein the one or more raised protrusions of said first textured section comprise one or more ridges concentric with a longitudinal axis of the the inner tubular member.

* * * * *